United States Patent [19]

Kamahori et al.

[11] Patent Number: 5,212,097
[45] Date of Patent: May 18, 1993

[54] METHOD FOR ANALYSIS OF CATECHOLAMINE

[75] Inventors: Masao Kamahori, Saitama; Mamoru Taki, Ibaraki; Junkichi Miura; Taro Nogami, both of Katsuta; Yoshio Watanabe, Hitachi, all of Japan

[73] Assignee: Hitachi, Ltd., Tokyo, Japan

[21] Appl. No.: 616,246

[22] Filed: Nov. 20, 1990

[30] Foreign Application Priority Data

Nov. 22, 1989 [JP] Japan .................................. 1-302187

[51] Int. Cl.$^5$ ........................................... G01N 33/00
[52] U.S. Cl. ................................... 436/111; 436/131; 436/172; 436/161
[58] Field of Search ..................... 436/111, 96, 89, 90, 436/129, 131, 172, 161, 816, 901; 210/650, 651, 656, 198.2, 635

[56] References Cited

U.S. PATENT DOCUMENTS

| | | | |
|---|---|---|---|
| 4,347,138 | 8/1982 | Ohno et al. | 210/651 |
| 4,705,757 | 11/1987 | Okhura | 436/111 |
| 5,011,608 | 4/1991 | Damjanovic | 436/161 |

FOREIGN PATENT DOCUMENTS

| | | |
|---|---|---|
| 3838385 | 5/1989 | Fed. Rep. of Germany . |
| 54-127393 | 10/1979 | Japan . |
| 60-205262 | 10/1985 | Japan . |

OTHER PUBLICATIONS

Mitsui et al., HPLC of Plasma Catecholamines . . . , J. Chromatography 344 (1985) 61–70.
Higa et al., Isolation of Catecholamines . . . , Anal Biochem 77 (1977) 18.
Degel et al., Effect of Pretreating Samples . . . , Clin. Chem. 33/1, (1967) 106–112.
De Jong, Selective Retention of Catecholamines . . . , J. Chromatography, 33 (1985) 43–53.
Hansson et al., Chromatographic Separation . . . , J. Chromatography, 161 (1978) 352–355.
Eriksson et al., Liquid Chromatographic . . . , J. Chromatography, 386 (1987) 1–9.
Shoup et al., Determination of Urinary Normethanephrine . . . , Clin. Chem., 27/7 (1977) 1268–1274.
Z. Naturforsch, vol. 45b, 1990, pp. 308–322 (partial English translation).
Analytica Chimica Acta, vol. 165, 1984.
Rinsho Kensa, 32, 12, 1988 (Clinical Examination).
Journal of Chromatography, vol. 344, 1985.
Analytical Biochemistry, vol. 77, 1977.
Journal of Chromatography, vol. 231, 1982.
Nippon Kagaku Kaishi, 1985, (7), 1040–1042.
Journal of Chromatography, vol. 155, 1978.
Protein, Nucleic Acid and Enzyme, vol. 26, No. 9, 1981.
Obstetrical and Gynecological Therapy, vol. 26, No. 9, 1981.

*Primary Examiner*—James C. Housel
*Assistant Examiner*—Lien Tran
*Attorney, Agent, or Firm*—Antonelli, Terry, Stout & Kraus

[57] ABSTRACT

Catecholamines in a living body fluid are analyzed by a process which involves reacting a living body fluid sample with a boron compound of the formula:

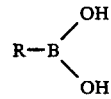

wherein R is hydroxyl, aryl or alkyl, to form a complex of the boron compound with a catecholamine; deproteinizing the reaction solution containing the complex; decomposing the complex to release the catecholamine; labeling the released catecholamine to form a labeled catecholamine; eluting the labeled catecholamine adsorbed on a separation column; and detecting the eluted, labeled catecholamine. Advantageously, this process enables catecholamines to be measured with a high recovery ratio and high accuracy by forming the catecholamines into a complex with a boron compound.

6 Claims, 8 Drawing Sheets (a)

(b)

METHOD FOR ANALYSIS OF CATECHOLAMINE

BACKGROUND OF THE INVENTION

This invention relates to a method for analyzing catecholamines contained in living body fluid, particularly to a method for analysis capable of treating catecholamines while maintaining them in a stable state and to a sample preparation liquid suitable for stabilization of catecholamines.

Catecholamine is a generic name for norepinephrine (NE), epinephrine (E), dopamine (DA), etc. and plays an important role as a neurotransmission substance or an adrenal medulla hormone. In order to study the functions of sympathetic nerves and adrenal medulla such as hypertonia, pheochromocytoma, sympathetic neuroblastoma, and the like, it is important to determine quantitative and qualitative changes of catecholamines in a living body sample such as blood, urine, etc.

In general, living body samples such as blood, pith liquid, etc., contain a higher concentration of protein and a lower content of catecholamines as compared with urine. Therefore, analysis of catecholamines in blood or pith liquid particularly requires a method of higher sensitivity than the methods conventionally used for analysis of catecholamines in urine. Moreover, due to the high protein concentration in blood or pith liquid, it is required to prevent the interference with the analysis by proteins. Furthermore, when the analysis is carried out by liquid chromatography, there is a problem of shortening of the life of the column therefor due to the high protein concentration.

In order to prevent the interference with the analysis by proteins and the deterioration of the column for liquid chromatography, it is general practice to carry out deproteinization treatment of a living body sample such as treatment with perchloric acid before liquid chromatography analysis. However, catecholamines are very unstable in neutral and alkaline conditions, and easily undergo a change such as oxidation. Since living body samples such as blood, pith liquid, etc., have a lower content of catecholamines than urine, the deproteinization treatment remarkably damages the catecholamines, so that it has not been possible to obtain any satisfactory analysis accuracy. It is known that catecholamines can be stabilized to some extent by adding an antioxidant such as EDTA, ascorbic acid, sodium thiosulfate, dithiothreitol, or the like to a living body sample and preserving the sample at not higher than $-20°$ C. However, the procedures therefor are made complicated, which complication has been an impediment to automation of catecholamine analysis. The foregoing matters have been discussed in Analytica Chimica Acta, 165 (1984), pp. 171-176 and "Rinsho Kensa (Clinical Examination)" 32, 12 (1988), pp. 1,522-1,527.

Catecholamines are determined generally by high-performance liquid chromatography. The assay thereof is carried out by fluorometry or an electrochemical method. The electrochemical method is susceptible to be influenced by the other components, and it is therefore not suitable for analysis of a trace amount of catecholamines. The fluorometry is classified into a DPE method using diphenylethylenediamine and THI method using trihydroxyindole. In the THI method, DA detection sensitivity is low, and catecholamines, e.g. in the blood cannot be analyzed. Therefore, the DPE method is the most suitable for analysis of a trace amount of catecholamines.

However, the optimum pH for a labeling reaction in the DPE method is pH 6.0 to 8.0, particularly in the vicinity of pH 7.0. In order to obtain high sensitivity, therefore, there is a dilemma in that the pH of the reaction solution prepared by mixing a sample with a labeling agent containing DPE is required to be brought close to the optimum pH, particularly to the vicinity of pH 7.0, whereas catecholamines are unstable under a pH around 7.0.

As the deproteinization method in the analysis of plasma catecholamines by the precolumn fluorescence HPLC method using DPE, studies have been made on ion-exchange column method which utilizes the difference in polarity between the proteins and the intended component for separating them, perchloric acid method which uses the precipitation of proteins by modification of the proteins with an acid, ultrafiltration method which uses the difference in size of molecule for the separation, and alumina column method which uses a column capable of selectively adsorbing catecholamines. However, the recovery ratios of these deproteinization methods are: 85% for ion-exchange column method, which shows the highest recovery ratio; 70 to 80% for perchloric acid method and ultrafiltration method; and 60 to 70% for alumina column method. Thus, the recovery ratios of these methods are all less than 90%. Therefore, these methods are unsatisfactory in their poor reproducibility and inability to carry out high-accuracy analysis. The foregoing matters are discussed in Journal of Chromatography, 344 (1985), pp. 61-70.

The above conventional techniques have not considered the stability of catecholamines during the preparation or analysis of the sample containing proteins to be removed. Nor have the above techniques considered the difficulty in controlling the pH of the reaction solution due to the difference between the optimum pH in the case of using the DPE method as a detection method and the pH at which catecholamines are stable. As a result, the above conventional techniques have a problem in the poor recovery ratio through the deproteinization and the reaction as a whole.

SUMMARY OF THE INVENTION

It is an object of this invention to provide a sample preparation liquid for catecholamine analysis, which stabilizes catecholamines and prevents them from being influenced by the other component present in a living body sample such as blood and from being oxidized.

It is another object of this invention to provide a method for analyzing catecholamines, which permits preparation of a sample in simple operation and has a high recovery ratio and accuracy.

The method of this invention comprises a step of forming a complex of a catecholamine with a specific boron compound before deproteinization treatment of a living body sample. It is known that a catecholamine and a boron compound form a complex. However, it had not been clear until the present inventors actually made experiments whether or not such a complex undergoes a change due to the deproteinization treatment and what the degree of the change is. Nor had it been clear until actual experiments of the present inventors whether satisfactory accuracy could be obtained.

Further, high-accuracy analysis can be carried out only when a catecholamine can be labeled highly efficiently after the complex of a catecholamine and a boron compound has been formed. Actual efficiency of the labeling reaction had not been clear until the present inventors attempted to make an experiment.

According to this invention, there are provided a method for analyzing catecholamines in a living body fluid, which comprises the steps of:

reacting a living body fluid sample with a boron compound of the formula,

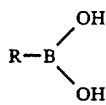

wherein R is hydroxyl, aryl or alkyl,
to form a complex of the boron compound with a catecholamine,
deproteinizing the reaction solution containing the complex, and
quantitatively determining the complex; and
a sample preparation liquid for catecholamine analysis which contains a boron compound of the formula,

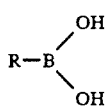

wherein R is hydroxyl, aryl or alkyl, the pH of the liquid being in a range of from 7.0 inclusive to 8.0 inclusive.

DETAILED DESCRIPTION OF THE INVENTION

Figure 1:
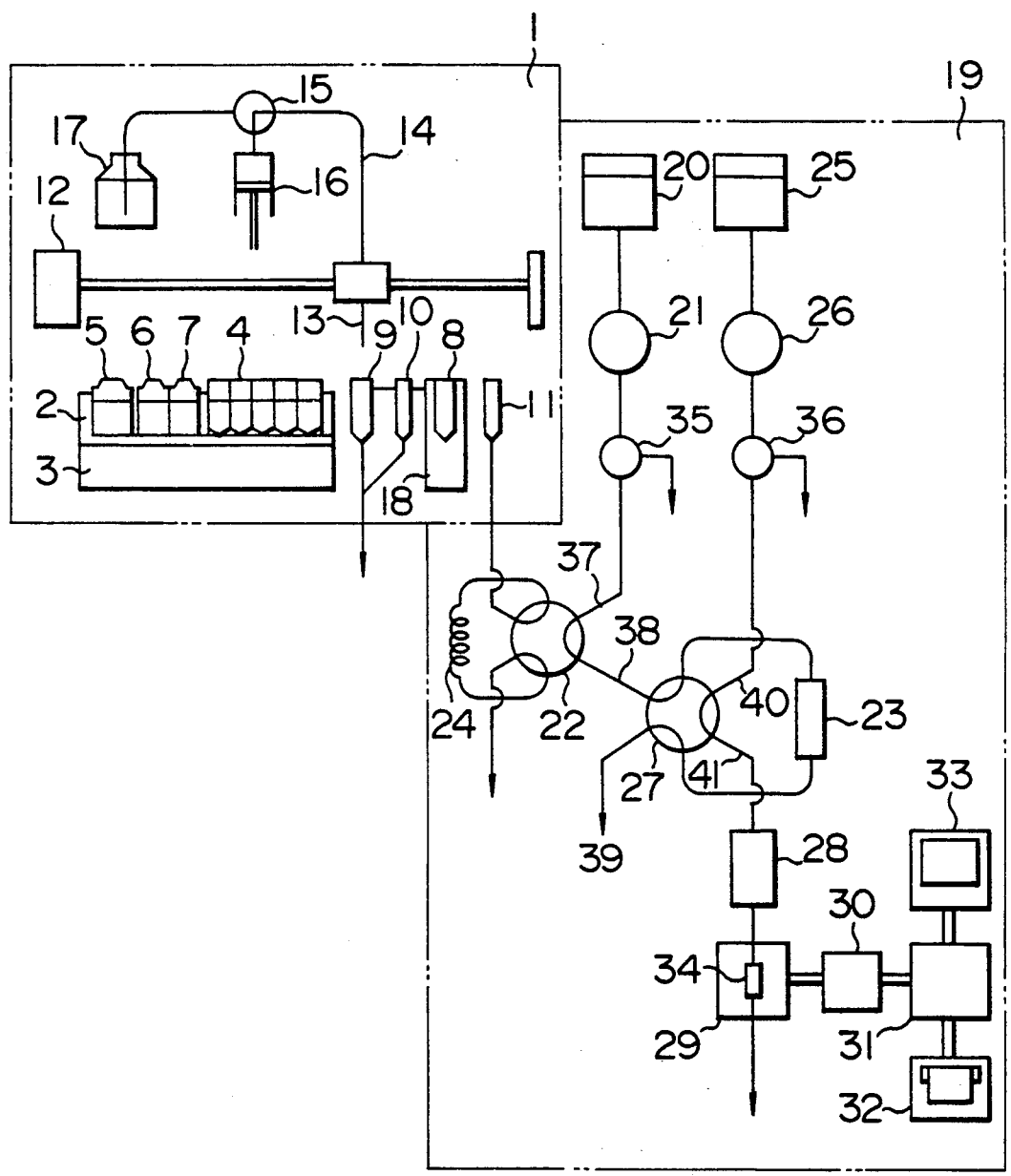
FIG. 1 shows a flow path system of an apparatus for analyzing catecholamines in one embodiment of this invention.

In the Figures, each numeral indicates the following: 1: autosampler, 2: sample rack, 4: sample container, 5: labeling reaction reagent, 8: a reaction container, 9: nozzle cleaning tank, 10: drain port, 11: injection port, 13: dispenser nozzle, 20: pretreatment liquid tank, 21: liquid transfer pump, 22: sample introducing valve, 23: precolumn, 24: measuring tube, 25: eluting liquid tank, 26: liquid transfer pump, 27: column switching valve, 28: separating column, 29: fluorophotometer, 31: control portion, 32: printer, and 33: CRT.

The boron compound of this invention is at least one member selected from compounds having a hydroxyl group, compounds having an aromatic group and compounds having an alkyl group. For example, preferred are boric acid, phenylboric acid, methylboric acid and ethylboric acid. And, the pH of a living body sample to which the boron compound has been added is preferably from 7.0 inclusive to 8.0 inclusive.

In the method of this invention, a boron compound having at least two hydroxyl groups is added to a living body fluid sample containing catecholamines which are unstable and easily oxidized, whereby a complex is formed, and the hydroxyl group of the catecholamine is protected. As a result, the catecholamine is stabilized. There is hence no necessity of carrying out complicated procedures for handling a living body sample containing catecholamines, to which, in an oxidative environment, an antioxidant such as EDTA or ascorbic acid has had to be added. Therefore, the measurement can be carried out with high accuracy without any suffering such as oxidation of catecholamines.

An analyzing apparatus embodying the analyzing method of this invention comprises an autosampler, an analyzing portion and a control portion. The analyzing portion comprises a precolumn flow path system, a separation column flow path system and a measuring operation portion. The autosampler is a sampler in which pretreatment such as batching-off and distribution of a prepared sample, addition of a reagent, a reaction, etc., can be carried out. In the precolumn flow path system, a sample introduced through a sample injector is flowed in a precolumn so that the column adsorbs the sample, whereby the sample is concentrated and impurities are removed. In the separation column flow path system, the sample concentrated with the precolumn is eluted with an eluting liquid and conveyed to a separation column through a column switching valve to separate specific components of the sample. The measuring operation portion comprises a detector to detect physical and chemical properties of the sample converted to a derivative, e.g. a fluorophotometer having a flow cell in the case of a fluorescence-labeled sample, and an operation display device for a measurement result. The control portion controls a series of analysis treatments.

As described above, this invention can be used as a general and simple treatment and measurement method to treat and measure catecholamines in living body samples such as serum, plasma, urine, etc.

Examples for a sample preparation method for catecholamine analysis in this invention will be explained hereinafter.

EXAMPLE 1

EDTA-sampled plasma was used as a sample. At first, a catecholamine preparation liquid A containing boric acid was prepared. The composition of the preparation liquid A is shown in Table 1.

TABLE 1

| | Composition |
|---|---|
| Preparation liquid A | 200 mM boric acid buffer, pH 7.3<br>1 mM ascorbic acid<br>1 mM EDTA |
| Preparation liquid B | 5 mM phenylboric acid<br>100% acetonitrile |

Figure 3:
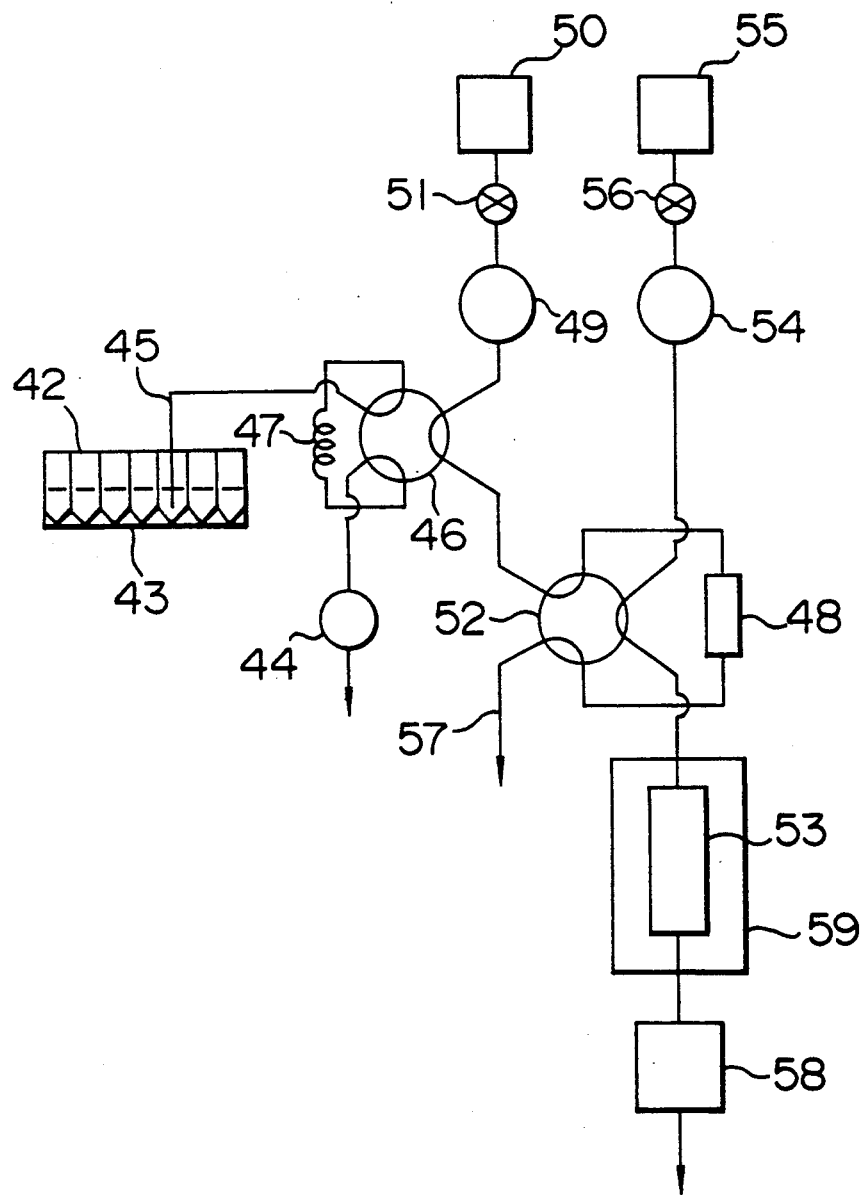
FIG. 3 shows a flow path system of an apparatus for analyzing catecholamines in another embodiment of this invention.

Then, 600 μl of the preparation liquid A was and fully mixed with 600 μl of the plasma. The resultant mixture was centrifugally (2,000 g, 20 minutes) deproteinized with an ultrafiltration membrane whose fractionation molecular weight is 10,000 (centricon-10, supplied by Amicon Inc.) to give a sample for catecholamine analysis (hereinafter referred to as the sample). The catecholamine analysis was carried out with an apparatus having a flow path shown in FIG. 3, which utilizes column switching method and fluorescence detection method by DPE. The measurement conditions were as shown in Table 2.

TABLE 2

| Description | Contents |
| --- | --- |
| Separation column | 4 mm I.D. × 150 mm (silica-ODS, particle diameter 3 μm) |
| Precolumn | 4 mm I.D. × 5 mm (cation exchange resin, CQK3OS, supplied by Mitsubishi Chemical Ltd.) |
| Pretreatment | 10 mM acetic acid buffer, pH 5.0<br>10 mM SDS<br>1 mM EDTA |
| Eluting liquid | 200 mM phosphoric acid buffer, pH 5.0/acetonitrile<br>10 mM SDS<br>1 mM EDTA (95/5, V/V) |
| Electrochemical detector | Applied voltage +650 mV |

In an autosampler 42, 500 μl each of the samples prepared as above are put in sample containers 43, and the containers are arranged. A sample (500 μl) is absorbed through a nozzle 45 with a pump 44 and introduced into a measuring tube 47 of a sample introducing valve 46. A pump 49 flows a pretreatment liquid 50 in a precolumn 48 through a valve 51, the sample introducing valve 46 and a column switching valve 52, and a pump 54 flows an eluting liquid 55 in a separation column 53 through a valve 56 and the column switching valve 52. In this state, the sample introducing valve is switched thereby to convey the sample in the measuring tube to the precolumn 48 with the pretreatment liquid 50, whereby the sample is adsorbed on the precolumn and concentrated, and at the same time impurities are removed with the flow of the pretreatment liquid and discharged through a discharge tube 57.

Figure 4A:
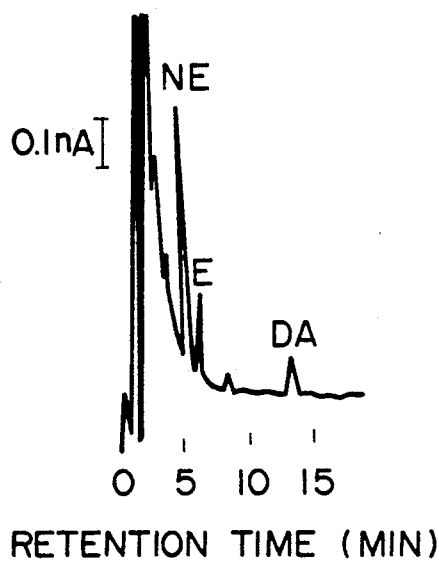
FIGS. 4(a), 6, 7 and 8 are chromatograms obtained in Examples of this invention.

Since a cation exchange resin is used as the precolumn, the amino group of the catecholamine is adsorbed on the precolumn, with keeping the hydroxyl group of the catecholamine in a stable state in the form of a complex with boric acid. Then, the column switching valve 52 is switched thereby to flow the eluting liquid 55 through the precolumn 48, whereby the sample is conveyed to the separation column 53 which is maintained at 40° C. with a column constant temperature tank 59, and each component separated is measured for a concentration with a detector 58. The flow rate each of the pretreatment liquid and the eluting liquid is 1 ml/minute. FIG. 4(a) shows the chromatogram obtained by carrying out the above measurement. In FIG. 4, the ordinate axis indicates current value and the abscissa axis indicates retention time. The above measurement was repeated ten times by using the identical sample to examine the reproducibility. The results are shown in Table 3. Further, a reference sample of catecholamines was added to the plasma which had been measured above, and the recovery ratios in Example 1 was measured. The results are shown in Table 4.

COMPARATIVE EXAMPLE (CONVENTIONAL METHOD)

Figure 4B:
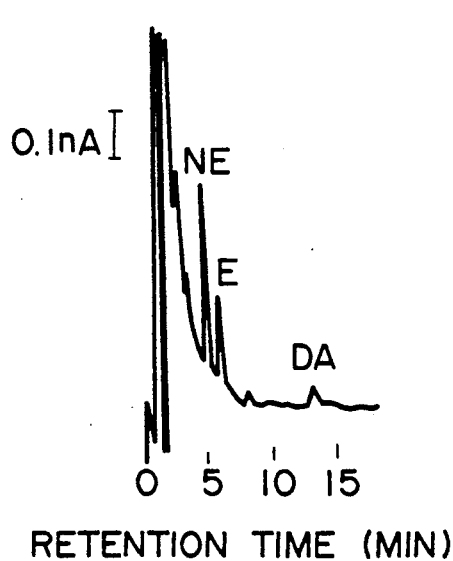
FIG. 4(b) is a chromatogram obtained according to a conventional method.

The sample preparation was carried out as follows: Fifty μl of 10 mM ascorbic acid and 50 μl of of 10 mM EDTA were added to 600 μl of EDTA-sampled plasma. Then, the pH of the mixture was adjusted to 2.0. Then, the mixture was centrifugally (2,000 g, 20 minutes) deproteinized with an ultrafiltration membrane whose fractionation molecular weight was 10,000 (Centricon-10, supplied by Amicon Inc.) to give a sample for catecholamine analysis. The same method and the same apparatus as in Example 1 were used to make measurement. The chromatogram obtained is shown in FIG. 4(b), in which the ordinate axis indicates current value and the abscissa axis indicates retention time. Further, by the use of the same sample as in Example 1, the reproducibility was examined in the same manner as in Example 1. The results are shown in Table 3. The recovery ratios were also measured. The results are shown in Table 4.

Figure 5:
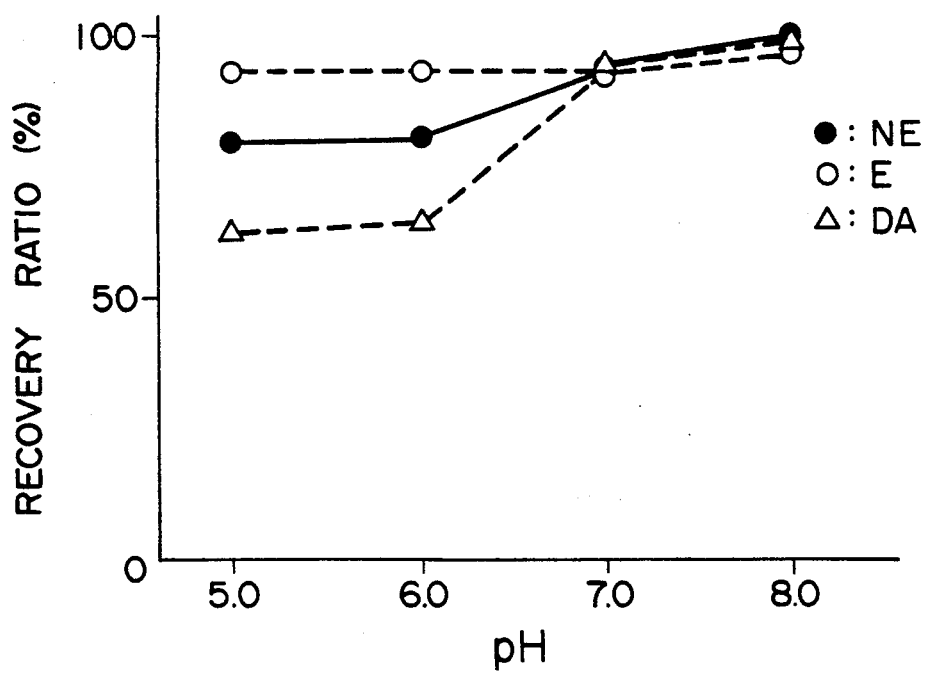
FIG. 5 shows the relationship between the pH of the sample preparation liquid used in Example and the recovery ratio.

As clearly shown in Tables 3 and 4, the method for preparation of a sample for catecholamine analysis according to this invention gives an unexpectedly higher accuracy and recovery ratio as compared with the conventional method. In particular, the recovery ratio of DA is remarkably improved, and therefore the measurement accuracy on DA is improved to the same level as that of the other components (NE and E). Also, the recovery ratio was measured by changing the pH of the preparation liquid A. The results are shown in FIG. 5, in which the ordinate axis indicates recovery ratio and the abscissa axis indicates pH of the preparation liquid A. When the preparation liquid had a pH of not less than 7.0 and not more than 8.0, the recovery ratios of NE, E and DA were not less than 95%. When the pH was below the range, the recovery ratios were low. The pH of a preparation liquid is therefore required to be not less than 7.0 and not more than 8.0.

TABLE 3

| | Concentration (pg/ml) | | | | | |
| --- | --- | --- | --- | --- | --- | --- |
| | NE | | E | | DA | |
| No. | Example 1 | Conventional method | Example 1 | Conventional method | Example 1 | Conventional method |
| 1 | 234 | 198 | 57 | 54 | 23 | 15 |
| 2 | 236 | 205 | 56 | 56 | 22 | 18 |
| 3 | 236 | 210 | 55 | 55 | 23 | 17 |
| 4 | 235 | 190 | 53 | 50 | 24 | 14 |
| 5 | 239 | 199 | 57 | 57 | 22 | 13 |
| 6 | 242 | 207 | 57 | 56 | 23 | 15 |
| 7 | 240 | 215 | 60 | 57 | 23 | 10 |
| 8 | 236 | 208 | 56 | 55 | 25 | 13 |
| 9 | 235 | 202 | 58 | 51 | 23 | 15 |
| 10 | 236 | 190 | 57 | 57 | 23 | 14 |
| $\bar{X}$ | 236.9 | 202.4 | 56.6 | 54.8 | 23.1 | 14.4 |
| S.D. | 2.56 | 8.26 | 1.84 | 2.49 | 0.876 | 2.22 |
| C.V. | 1.08% | 4.08% | 3.25% | 4.54% | 3.79% | 15.4% |

TABLE 4

|  | Recovery ratio (%) | | |
| --- | --- | --- | --- |
|  | NE | E | DA |
| Conventional method | 85.3 | 95.1 | 63.7 |
| Example 1 | 98.9 | 98.6 | 100.3 |
| Example 2 | 99.0 | 98.1 | 102.1 |

EXAMPLE 2

This Example is to describe another embodiment of the method for preparation of a sample for catecholamine analysis according to this invention. EDTA-sampled plasma was used as a sample. At first, phenylboric acid was dissolved in acetonitrile to prepare a sample preparation liquid B for catecholamine analysis. The composition of the preparation liquid B is shown in Table 1. Then, 400 μl of the preparation liquid B was added to 400 μl of the plasma and fully mixed therewith. Proteins modified with acetonitrile were centrifugally (5,000 g, 20 minutes) precipitated and separated. 500 Microliters of the resultant supernatant was used as a sample for catecholamine analysis. The sample was measured in the same manner as in Example 1. A reference sample of catecholamines was added to the plasma which had been measured above, and the recovery ratios were measured. The results are shown in Table 4. Table 4 shows that the recovery ratios of NE, E and DA are all more than 98% and that the recovery ratios are remarkably improved over the conventional method. For this Example, acetonitrile was used as an organic solvent; however, the other organic solvents usually used for the deproteinization method may be used in this invention. Specific examples of such an organic solvent are ethanol, methanol and acetone.

EXAMPLE 3

Figure 9:
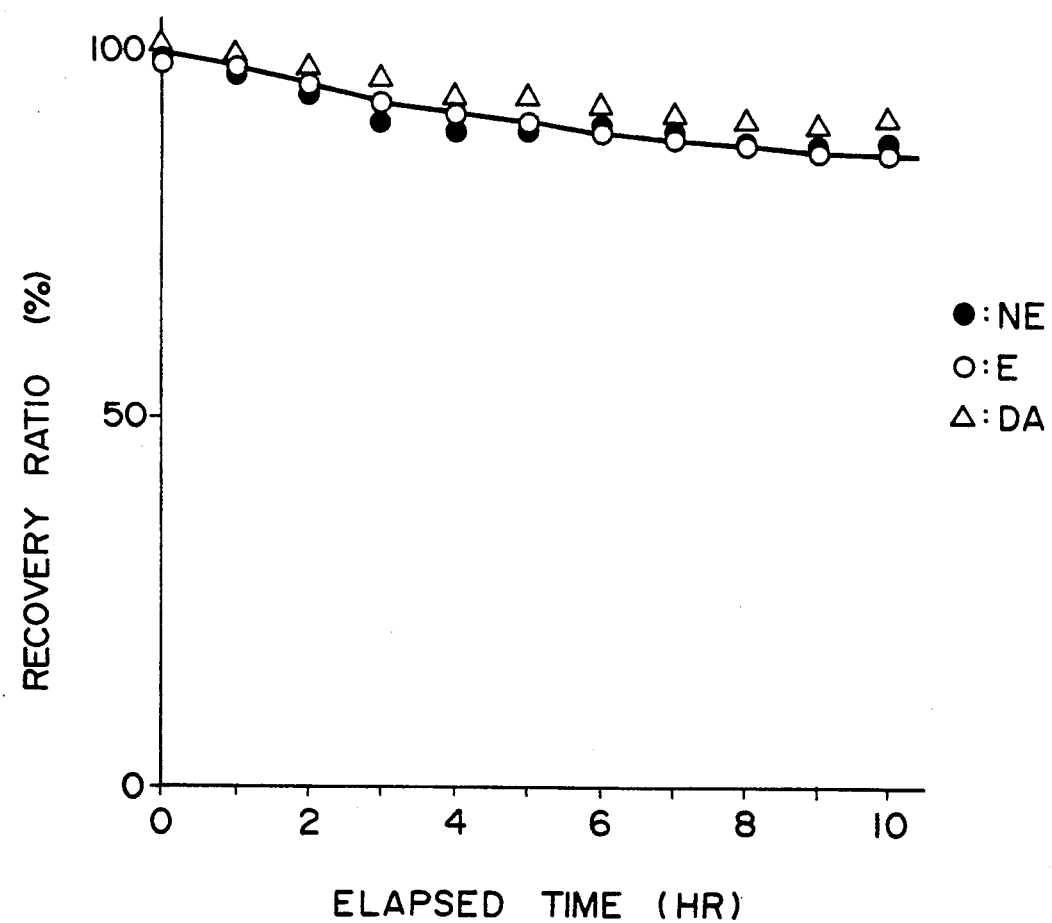
FIG. 9 shows a curve of recovery ratios of catecholamines vs. elapsed time of storage.

This Example is to describe the stability of a sample when a boron compound has been added to the sample not before but after the deproteinization in the sample preparation method for catecholamine analysis. As a sample, a reference sample of catecholamines was added to EDTA-sampled plasma, and the resultant mixture was cooled to 4° C. and stored. Then, in each of predetermined time intervals, 400 μl of acetonitrile was added to and fully mixed with 400 μl of the above sample, and the resultant mixture was centrifuged (5,000 g, 20 minutes) to precipitate and separate proteins. Then, 50 μl of 30 mM phenylboric acid solution was added to 500 μl of the resultant supernatant to prepare a sample for catecholamine analysis. The measurement was carried out in the same manner as in Example 1. The results are shown in FIG. 9, in which the ordinate axis indicates recovery ratio and the abscissa axis indicates elapsed time. FIG. 9 shows that the recovery ratio decreases as the storage time passes. In view of this results, the boron compound is required to be added before the deproteinization of the plasma sample.

EXAMPLE 4

This Example is to describe another embodiment of the method for preparation of a sample for catecholamine analysis. Urine was sampled and charged into a container into which an aqueous solution of hydrogen chloride had been charged. The resultant mixture had pH of 1 to 2. The mixture was preserved as such and was used as a sample. At first, a sample preparation liquid C (hereinafter referred to as diluent C) for catecholamine analysis was prepared. Table 5 shows the composition of the diluent C. Twenty microliters of the above preserved urine sample was diluted with the diluent C whose volume was 100 times as large as that of the preserved urine. The measurement was carried out in the same manner as in Example 1. A reference sample of catecholamines was added to the preserved urine which had been measured above, and the recovery ratios thereof were measured. Table 6 shows the results. Further, there were prepared sample preparation liquids D and E (hereinafter referred to as diluents D and E) for catecholamine analysis. The diluents D and E contained phenylboric acid or ethylboric acid, respectively, each of which was capable of forming a complex with a catecholamine. Table 5 shows the compositions of the diluents D and E. The recovery ratios were measured by using samples prepared from the diluents D and E. The results are shown in Table 6. As shown in Table 6, the recovery ratios of NE, E and DA were as greater than 95% when any one of the diluents C, D and E was used. The above results clearly show not only that the boron compound to be added to the preparation liquid is not limited to a boric acid buffer, but also that boron compounds having at least two hydroxyl groups capable of forming a complex with a catecholamine, e.g. phenylboric acid, ethylboric acid, etc., can give like effects.

TABLE 5

|  | Composition |
| --- | --- |
| Diluent C | 100 mM boric acid buffer, pH 7.3<br>1 mM EDTA |
| Diluent D | 100 mM Tris-HCl buffer, pH 7.3<br>1 mM EDTA<br>5 mM phenylboric acid<br>5% acetonitrile |
| Diluent E | 100 mM Bicine buffer, pH 7.3<br>1 mM EDTA<br>5 mM ethylboric acid |

TABLE 6

|  | Recovery ratio (%) | | |
| --- | --- | --- | --- |
|  | NE | E | DA |
| Diluent C | 99.6 | 97.8 | 102.7 |
| Diluent D | 96.2 | 95.9 | 99.8 |
| Diluent E | 99.7 | 98.0 | 100.3 |

EXAMPLE 5

An apparatus for catecholamine analysis will be explained by reference to FIG. 1. In the flow path system of FIG. 1, an autosampler 1 is provided with a sample stage 3 so that a sample rack 2 is fitted thereto. Arranged on the sample rack 2 is a sample container 4 containing a sample to be analyzed, and at the same time, arranged thereon are containers which individually contain fluorescence labeling reagent 5, an internal reference liquid 6 and a reference sample 7. The sample is prepared by treating plasma, urine, etc., according to the sample preparation method of this invention, and used as such. And, arranged adjacent to the sample stage 3 are a reaction vessel 8, a nozzle cleaning tank 9, a drain port 10 and an injection port 11, and these are fixed in place. A driving mechanism 12 has an XYZ driving function and can move a dispenser nozzle 13 to the positions of the container on the above sampler, the port, etc., by driving it three-dimensionally. The upper end of the dispenser nozzle 13 is connected to a dispenser pump 16 and a cleaning tank 17 by means of a capillary 14 such as a Teflon tube through a three way valve 15. The dispenser pump 16 is a pulse motor-driven syringe pump. A constant temperature block 18 is provided to keep the temperature of the reaction vessel 8 under predetermined conditions. And, the sample stage 3 is provided with a cooling device to keep the sample and the reagent on the sample rack 2 at a low temperature during the analysis.

An analysis portion 19 comprises a precolumn flow path system to concentrate the sample and remove impurities, a separation column flow path system to separate sample components, and a measuring operation portion. In the precolumn flow path system, a pretreatment liquid of a pretreatment liquid tank 20 is conveyed at a constant rate with a pump 21, and flowed in a precolumn 23 through a sample introducing valve 22. The sample introducing valve 22 is provided with a measuring tube 24 to measure a predetermined amount of a pump liquid injected from the injection port 11 and introduce it into the analysis portion. In the separation column flow path system, an eluting liquid of an eluting liquid tank 25 is conveyed at a constant rate with a pump 26, and is flowed in a separation column 28 through a column switching valve 27. The column switching valve 27 is switched thereby to flow the eluting liquid through the precolumn 23, whereby the eluting liquid conveys the sample treated in the precolumn to the separation column 28. The measuring operation portion comprises a fluorophotometer 29 to measure the fluorescent light intensities of sample components eluted from the separation column 28, an A/D transducer 30 to process and display the measurement results, a control portion 31, a printer 32 and a CRT 33. The fluorophotometer 29 is provided with a flow cell 34. In addition, switch cocks 35 and 36 are provided to purge liquids within the pumps 21 and 26 when necessary.

The operation of the analysis apparatus of this Example is explained hereinafter.

Figure 2:
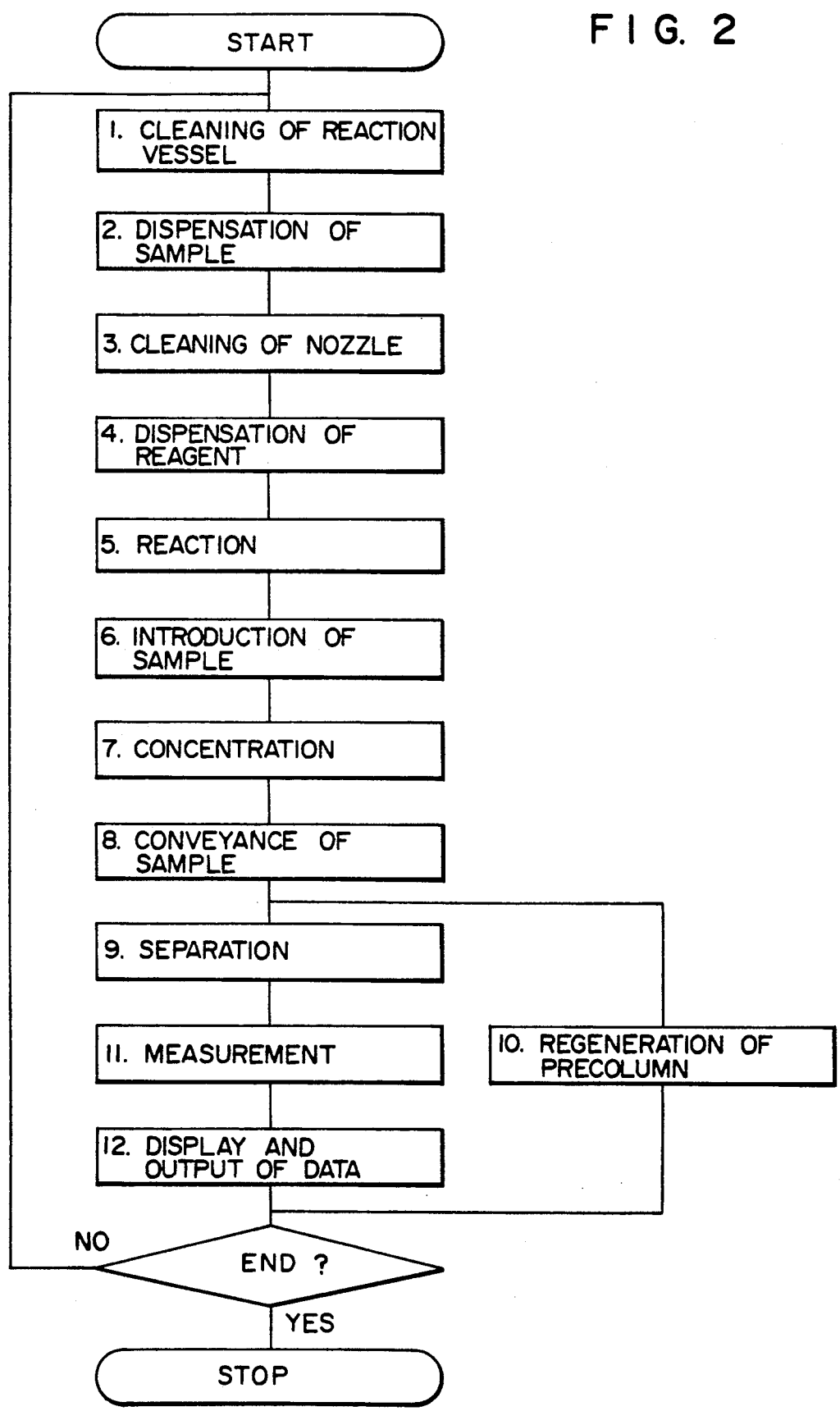
FIG. 2 is an analysis flow chart in the embodiment shown in FIG. 1.

When the above analysis apparatus is used, the sample is treated in the order of fluorescence labeling of the sample prepared on the autosampler according to the sample preparation method for catecholamine analysis, concentration and removal of impurities in the precolumn, and separation and measurement of sample components in the separation column. FIG. 2 shows the flow chart of the operation. The apparatus is operated according to the following steps.

(1) Cleaning of Reaction Vessel

The nozzle 13 is moved to the position of the reaction vessel 8, and the dispenser pump 16 is operated to inject a cleaning liquid in the cleaning liquid tank into the reaction vessel. The cleaning liquid is injected in a larger amount than the volume of the reaction vessel, and the excess amount of the cleaning liquid is overflowed and discharged through the drain port 10. Then, the nozzle is moved down to the bottom of the reaction vessel to suck up the cleaning liquid, and then moved to the drain port to discharge the sucked cleaning liquid. In order to prevent diffusion of the sucked dirty cleaning liquid into a fresh cleaning liquid, a small amount of air bubbles may be sucked and present in the end portion of the nozzle in advance of the above suction operation. In addition, the operation of forming a barrier with sucked air bubbles before the suction may be sometimes required in the case of suction of a sample and a reagent at later steps. However, the explanation for such a case at later steps will be omitted. The cleaning of the reaction vessel is finished by repeating the above operation a plurality of times, e.g. three times.

(2) Dispensation of Sample

The nozzle 13 is moved to the position of the internal reference liquid 6, moved down to such a predetermined amount thereof, moved to the position of the sample container 4 to suck a predetermined amount of a sample, and moved to the position of the reaction vessel to dispense the sucked sample and the internal reference liquid into the reaction vessel 8. The internal reference liquid is a reference liquid used to correct the variation of recovery ratio, etc., caused by the entire system, particularly by the column. This Example uses isoproterenol as a reference substance.

(3) Cleaning of Nozzle

The nozzle 13 is moved to the drain port 10, and a cleaning liquid is discharged to wash away the stain which the internal reference liquid and the sample have caused on the internal wall of the nozzle. Then, the nozzle 13 is moved to the nozzle cleaning tank 9 and moved down into the tank, and a cleaning liquid is discharged to clean the exterior of the nozzle top.

(4) Dispensation of Reagent

The nozzle 13 is moved to the position of the container of the reagent 5 to suck a predetermined amount of a reagent and inject it into the reaction vessel 8, whereby the reagent is incorporated into the sample and the internal reference liquid which have been injected in advance. The incorporation is carried out by preliminarily sucking air in the nozzle, inserting the nozzle into the vessel and discharging the air, or by externally vibrating the vessel mechanically or electrically. In the case of an easily miscible liquid and a comparatively large discharge amount, the incorporation can be sometimes made at a high discharge rate.

(5) Reaction

A mixed solution of the above sample with the above reagent (hereinafter referred to as a sample solution) is left to stand in the reaction vessel for a predetermined period of time to carry out a reaction and fluorescence labelling.

In this case, the diol group of catecholamines, which is unstable and easily oxidized at a neutral pH, are considered to have been protected by forming a complex with the hydroxyl groups of a boron compound. For example,

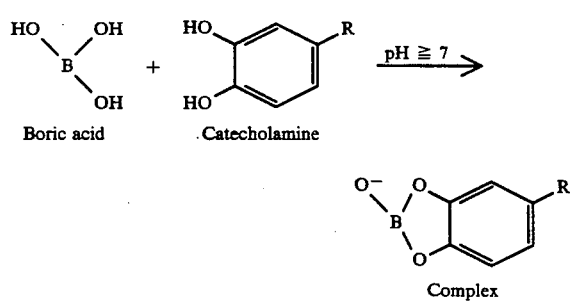

At the fluorescence labeling, potassium ferricyanide mixed with the labeling agent oxidizes the diol moiety of catecholamines at first whereby the complex is decomposed. The diol group of the released catecholamines then reacts with the fluorescence labeling agent (e.g. DPE). For example,

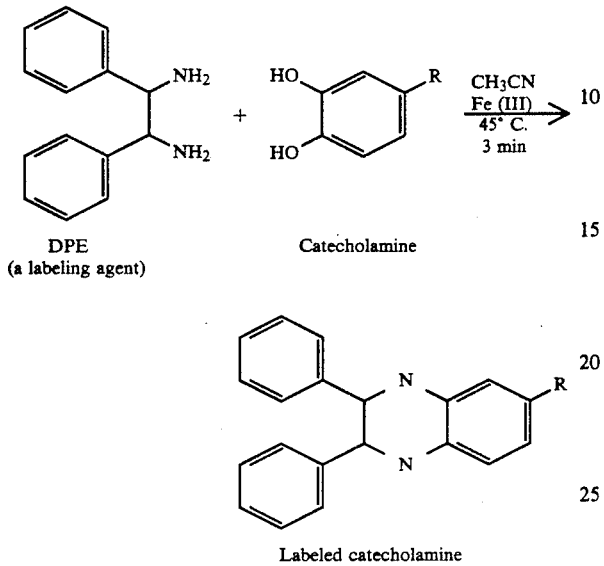

(6) Introduction of Sample

By the nozzle 13, the reacted sample solution was sucked and inserted into the cleaning port 11 to inject the solution into the measuring tube 24 of the sample introducing valve 22. Then, the sample introducing valve 22 is switched to interconnect the measuring tube 24 with the flow paths 37 and 38, whereby the solution is conveyed to the precolumn with a flow of the pretreatment liquid.

(7) Concentration

The sample solution is flowed in the precolumn with a flow of the pretreatment liquid, whereby the sample is concentrated by adsorption on the interior of the precolumn, and at the same time, impurities which are to interfere with the analysis are removed from the sample and discharged through a discharge port 39.

(8) Conveyance of Sample

The column switching valve 27 is switched to interconnect the precolumn 23 with the flow paths 40 and 41, whereby the eluting liquid flows through the precolumn 23 to dissociate the sample concentrated in the precolumn and convey it to the separation column 28, and the separation starts. When the sample is all moved to the flow path 41, the column switching valve 27 is switched (as shown in FIG. 1), whereby the eluting liquid is flowed not through the precolumn 23 but directly to the separation column 28, and the pretreatment liquid flows in the precolumn 23.

(9) Separation

The eluting liquid is flowed on in the separation column 28 to separate the intended components.

(10) Regeneration of Precolumn

While the above separation of the sample components is carried out, the pretreatment liquid is flowed in the precolumn 23 to bring it into a state in which a fresh sample can be introduced.

(11) Measurement

The sample components separated and eluted in the separation column 28 successively flow to the flow cell 34 of the fluorophotometer 29, where the fluorescent light intensities thereof are detected and processed to determine the concentrations of the components.

(12) Display and Output of Data

The data obtained above is displayed and output by means of the printer 32 or CRT 33.

EXAMPLE 6

Figure 6:
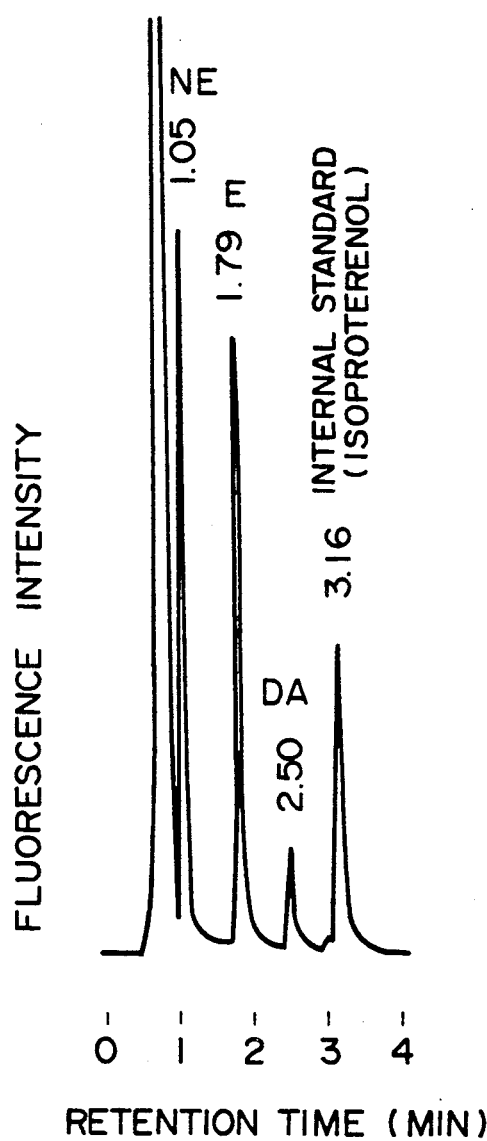

This Example is to describe the method for analysis of catecholamines. The measurement was carried out by using a catecholamine analyzing apparatus based on the flow path shown in FIG. 1. EDTA-sampled plasma was used as a sample. The sample preparation procedure in Example 1 was repeated to give 500 µl of a sample for catecholamine analysis. This sample for catecholamine analysis in the amount of 500 µl was charged into a sample container 4. A reagent 5 for fluorescence labeling, an internal reference solution 6 and a reference sample 7 were mounted on a sample rack 2. The measurement conditions are shown in Table 7. The analysis was proceeded with on the basis of the flow chart shown in FIG. 2. In a reaction vessel, 500 µl of the sample 450 µl of the reagent for fluorescence labeling and 50 µl of the internal reference solution were mixed with each other, and the resultant mixture was allowed to react at a temperature of 45° C. for 3 minutes. After the reaction, 500 µl of the reaction mixture was injected into a measuring tube 24. The flow rate each of a pretreatment liquid and an eluting solution was 1 ml/min. The chromatogram obtained is shown in FIG. 6, in which the ordinate axis indicates fluorescence intensity of catecholamine derivative and the abscissa axis indicates retention time. Table 8 shows the test results of reproducibility and recovery ratio obtained by using the same sample. The measurement using this catecholamine analysis apparatus showed good results that C.V. values were less than 3% and that the recovery ratios were more than 98%. Further, the measurement using the samples prepared in Examples 2 and 3 showed good results on both accuracy and recovery ratio.

TABLE 7

| Description | Content |
| --- | --- |
| Reagent for fluorescene labeling | 20 mM 1,2-DPE<br>2 mM potassium ferricyanide<br>40% acetonitrile |
| Internal reference solution | 10 pmol/ml isoproterenol |
| Reference solution | 1 pmol/ml NE, E, DA |
| Separation column | 4.6 mm I.D. × 60 mm (silica ODS, particle diameter 3 µm) |
| Precolumn | 4.0 mm I.D. × 5 mm (internally antiphase filler, L-1180, supplied by Chemical Products Inspection Association) |
| Pretreatment liquid | 0.1 M NaCl<br>0.1 mM EDTA<br>5% acetonitrile |
| Eluting liquid | Acetonitrile/methanol/50 mM boric acid 10 mM SOS, pH 7.3 |
| Detector | Fluorescent monitor (F-1050, supplied by Hitachi) ex. 345 nm, Em 485 nm |

TABLE 8

| No. | Concentration (pg/ml) | | |
|---|---|---|---|
| | NE | E | DA |
| 1 | 235 | 57 | 23 |
| 2 | 237 | 56 | 22 |
| 3 | 237 | 56 | 23 |
| 4 | 238 | 56 | 23 |
| 5 | 237 | 57 | 24 |
| 6 | 240 | 58 | 23 |
| 7 | 238 | 60 | 23 |
| 8 | 237 | 56 | 24 |
| 9 | 237 | 55 | 23 |
| 10 | 239 | 56 | 23 |
| X̄ | 237.5 | 56.7 | 23.1 |
| S.D. | 1.35 | 1.42 | 0.57 |
| C.V. | 0.57% | 2.50% | 2.46% |
| Recovery ratio | 99.7% | 98.6% | 100.3% |

EXAMPLE 7

Figure 7:
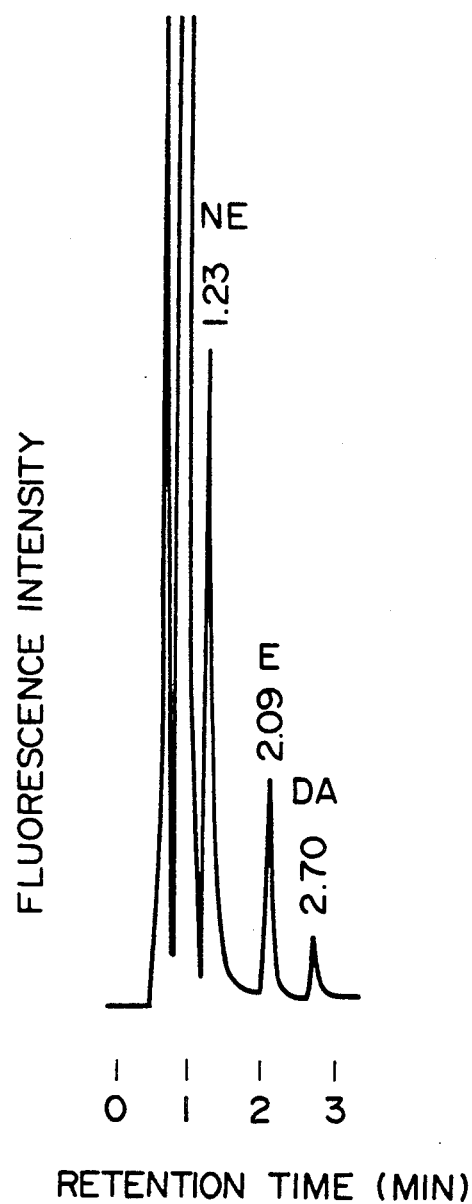

This Example is to describe another embodiment of the method for analysis of a catecholamine. EDTA-sampled plasma was used as a sample. The sample preparation was carried out in the same manner as in Example 1 based on this invention. An apparatus for the measurement was the apparatus for catecholamine analysis equipped with the flow path system shown in FIG. 1. The analysis was proceeded with on the basis of the flow chart shown in FIG. 2. In order to improve separability, this Example used a 4.6 mm I.D ×80 mm (silica ODS, particle diameter 3 μm) column as a separation column. Further, in order to keep the analysis time within three minutes, no internal reference substance was added. The quantitative determination was carried out by an external reference method using concentration calculation on the basis of measurement values on a reference sample containing 1 pmol/ml of each of NE, E and DA. The other measurement conditions are as shown in Table 7. The results of the measurement of this Example 7 using an external reference method as a concentration calculation method showed that the C.V values were less than 4% and that the recovery ratios of NE, E and DA were more than 96%. Thus, these results were as good in accuracy and recovery ratio as those in Example 6 using an internal reference method. The chromatogram obtained is as shown in FIG. 7, in which the ordinate axis indicates fluorescence intensity and the abscissa axis indicates retention time. FIG. 7 shows that the peak of NE exhibits better separation than that of NE in FIG. 6.

EXAMPLE 8

Figure 8:
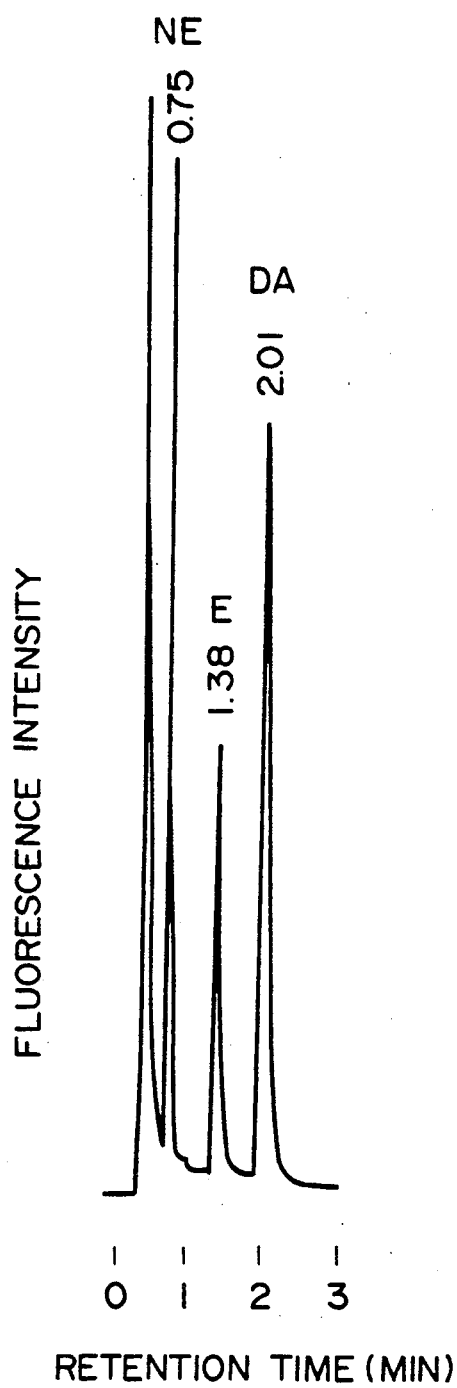

This Example is to describe an embodiment of the method for catecholamine analysis according to this invention. As a sample, there was used preserved urine having pH of 1 to 2. The sample preparation was carried out in the same manner as in Example 4 based on this invention. The analysis was carried out by using an apparatus for catecholamine analysis equipped with the flow path system shown in FIG. 1. The analysis was proceeded with on the basis of the flow chart shown in FIG. 2. In order to keep the analysis time within 2.5 minutes, a 4.0 mm I.D. ×50 mm (silica ODS, particle diameter 2.5 μm) column was used as a separation column. The quantitative determination was carried out by an external reference method using concentration calculation on the basis of measurement values on a reference sample containing 1 pmol/ml of each of NE, E and DA. The other measurement conditions are as shown in Table 7. The chromatogram obtained is shown in FIG. 8, in which the ordinate axis indicates fluorescence intensity and abscissa axis indicates retention time. As shown in FIG. 8, three catecholamine components (NE, E and DA) in urine could be analyzed within 2.5 minutes.

In this invention, a catecholamine in living body sample such as plasma, urine, etc., can be stabilized by forming it into a complex with a boron compound having at least two hydroxyl groups such as boric acid, and the catecholamine is hence made insusceptible to influence, e.g. oxidation, of the other substances in the living body samples. Therefore, this invention has advantageous in that the catecholamines can be measured with a high recovery ratio and high accuracy.

Further, the catecholamines which have been hard to measure by high-performance liquid chromatography with good accuracy can be accurately measured. Therefore, as another advantage, this invention can provide an apparatus for catecholamine analysis which can be used, e.g. for routine work in mass health examination and usual examination.

What is claimed is:

1. A method for analyzing catecholamines in a living body fluid, which comprises the steps of:
   (1) reacting prior to deprofeinization a living body fluid sample with a boron compound of the formula,

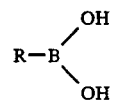

wherein R is hydroxyl, phenyl, methyl or ethyl to form a reaction solution which includes complexes of the boron compound with catecholamines,
   (2) deproteinizing the reaction solution containing the complexes,
   (3) decomposing the complexes to release the catecholamines,
   (4) labeling the released catecholamines to form labeled catecholamines,
   (5) allowing the labeled catecholamines to adsorb on a precolumn packed with a cation exchange resin and removing impurities by passing an appropriate pretreatment liquid through the precolumn,
   (6) eluting the labeled catecholamines adsorbed on the precolumn,
   (7) passing the eluting liquid including labeled catecholamines to a separation column
   (8) eluting the separate labeled catecholamines,
   (9) detecting the eluted, labeled catecholamines.

2. The method of claim 1, wherein the step of reacting the living body fluid sample with the boron compound includes the step of keeping the pH of the reaction solution within a range of from 7.0 inclusive to 8.0 inclusive.

3. The method of claim 1, wherein the step of the deproteinization is carried out by using an ultrafiltration membrane.

4. The method of claim 1, wherein the step of the deproteinization is carried out by using an organic solvent.

5. The method for analyzing catecholamines in a living body fluid of claim 1, wherein the step (3) is carried out by using potassium ferricyanide.

6. The method of claim 1, wherein the step of labeling the released catecholamines to form labeled catecholamines is carried out with diphenylethylenediamine.

* * * * *